United States Patent
Gilbert

(10) Patent No.: US 6,961,622 B2
(45) Date of Patent: Nov. 1, 2005

(54) DEVICE FOR SURFACE STIMULATION OF ACUPUNCTURE POINTS

(75) Inventor: Bruce R. Gilbert, Great Neck, NY (US)

(73) Assignee: The Russel Group LLC, Great Neck, NY (US)

( * ) Notice: Subject to any disclaimer, the term of this patent is extended or adjusted under 35 U.S.C. 154(b) by 337 days.

(21) Appl. No.: 10/285,120

(22) Filed: Oct. 31, 2002

(65) Prior Publication Data

US 2004/0088036 A1 May 6, 2004

Related U.S. Application Data

(63) Continuation of application No. PCT/US02/08480, filed on Mar. 19, 2002.
(60) Provisional application No. 60/277,367, filed on Mar. 20, 2001.

(51) Int. Cl.[7] .................................................. A61N 1/04
(52) U.S. Cl. ...................................................... 607/148
(58) Field of Search ........................... 607/46, 142, 148, 607/149, 152, 153; 600/382–384, 386, 391, 392, 393, 397; 128/907

(56) References Cited

U.S. PATENT DOCUMENTS

| 2,223,447 A | 12/1940 | Hathaway |
| 3,107,672 A | 10/1963 | Hoffmann |
| 3,424,165 A | 1/1969 | Moss |
| 3,911,910 A | 10/1975 | Oseau |

(Continued)

OTHER PUBLICATIONS

Alkaissi, A., et al. "Effect and placebo effect of acupressure (P6) on nausea and vomiting after outpatient gynaecological surgery", *ACTA Anaesthesiologica Scand* 1999, 43: 270–274.

(Continued)

Primary Examiner—Jeffrey R. Jastrzab
(74) Attorney, Agent, or Firm—Ladas and Parry LLP

(57) ABSTRACT

A device, which is preferably disc shaped, has two primary layers. A first layer has one side, which is the lower side in use, for adhering to a patient's skin surface, a second, upper layer on the underside of which electrical circuitry is printed or affixed so that the electrical circuitry is sandwiched between the layers. The device can be made in several sizes to accommodate patient size and location of the acupuncture point to be stimulated. Two distinct forms of the device are presented: a single use and a reusable device for. In the single use device, the first, lower layer is preferably a foam with non-conductive adhesive on both sides: the bottom side for adhering to the skin and the top side for adhering to the upper polyester disc. The holes through this lower foam layer include, preferably, eight holes spaced concentrically about one central hole in the middle of the lower foam layer. All these holes are, preferably, overfilled with an electrically conductive gel that projects from the lower foam layer. The conductive circuitry preferably printed on the underside of the upper layer provides a series connection to the gel in each of the eight concentric holes and a separate connection to the gel in the center hole when the upper layer is adhered to the lower layer. The printed circuitry may be a silver/silver chloride polymer film, also provides for a tab(s) which can be permanently or temporarily affixed to an integral or remote simulator through direct contact or wire leads. In the reusable device a pressure-sensitive adhesive material forms the lower layer which allows for multiple applications to a patient's skin. The adhesive lower layer is transparent to show the circular central electrode the annular electrode. The electrodes are preferably silver/silver chloride polymer film. In either configuration, metal core insulated leads can be use for electrical connection with the opposite ends of the leads connected to jacks for connection to an impulse stimulator or can end in electrically conductive tabs.

28 Claims, 6 Drawing Sheets

U.S. PATENT DOCUMENTS

| | | | |
|---|---|---|---|
| 4,082,087 A | * | 4/1978 | Howson ..................... 600/391 |
| 4,398,545 A | | 8/1983 | Wilson |
| 4,715,367 A | | 12/1987 | Crossley |
| 4,907,601 A | | 3/1990 | Frick |
| 4,915,110 A | | 4/1990 | Kitov |
| 4,981,146 A | | 1/1991 | Bertolluci |
| 5,450,845 A | | 9/1995 | Axelgaard |
| 5,785,040 A | | 7/1998 | Axelgaard |
| 5,950,635 A | | 9/1999 | Garcia-Rill |
| 5,957,951 A | | 9/1999 | Cazaux |
| 6,272,383 B1 | | 8/2001 | Grey |

OTHER PUBLICATIONS

Al–Sadi, M., et al. "Acupuncture in the prevention of postoperative nausea and vomiting", *Anaesthersia,* 1997, 52, pp. 658–661.

Chen, L., et al., "The effect of location of transcutaneous electrical nerve stimulation on postoperative opioid analgesic requirement: acupoint versus nonacupoint stimulation", *Anesth Analg,* 1998, 87(5); p. 1129–34.

Christensen, P. A., et al., Electroacupuncture and postoperative pain, *British Journal. Anaesthesia,* 1989, 62(3): p. 258–62.

De Aloysio, D., et al., "Morning sickness control in early pregnancy by Neiguan point acupressure", *Obstetrics and Gynecology,* 1992, 80(5): p. 852–4.

Dundee, J. W., et al., "Acupuncture prophylaxis of cancer chemotherapy–induced sickness" *Journal of the Royal Society of Medicine,* 1989, 82(5): p. 268–71.

Dundee, J. W. "Effect of Stimulation of the P6 Antiemetic Point on Postoperative Nausea and Vomiting", *British Journal Anaesthesia.,* (1989), 63, 612–18.

Helms, J. M., "Acupuncture for the Management of Primary Dysmenorrhea" *Obstetrics and Gynecology,* 1987, 69(1): p. 51–6.

Kho, H. G., et al., "The use of acupuncture in the treatment of erectile dysfunction", *International Journal of Impotence Research,* 1999, 11(1): p. 41–6.

Lee, Anna, et al., "The Use of Nonpharmacologic Techniques to Prevent Postoperative Nausea and Vomiting: A Meta–Analysis", *Anesth Analg,* 1999;88:1362–9.

NIH Consensus Statement, *Acupuncture,* National Institutes of Health, 1997, vol. 15, No. 5, p. 1–34.

Omura, Y., "Simple custom–made disposable surface electrode system for non–invasive 'electro–acupuncture' or TNS and its clinical applications including treatment of cephalic hypertension and hypotension syndromes as well as temporo–mandibular joint problems, tintinitus, shoulder and lower back pain, etc.", *Acupuncture and Electro–Therapeut. Res., Int. J.,* 1981, 6(2–3): p. 109–34.

Schlager, A., et al., Laser stimulation of acupuncture P6 reduces postoperative vomiting in children undergoing strabismus surgery, *British Journal of Anaesthesia,* 1998, 81(4): p.

Shen, J., et al., "Electroacupuncture for Control of Myeloablative Chemotherapy Induced Emesis: A Randomized Controlled Trial", *JAMA,* 2000, 284(21): p. 2755–2761.

Siterman, S., et al., "Effect of acupuncture on sperm parameters of males suffering from subfertility related to low sperm quality", *Archives of Andrology,* 1997, 39(2): p. 155–61.

Slotnick, R. Nathan, "Safe, Successful Nausea in Suppression in Early Pregnancy with P–6 Acustimulation", *The Journal of Reproductive Medicine,* 4(9) 2001 p. 811–814.

Tougas, G., et al., "Effect of Acupuncture on Gastric Acid Secretion in Healthy Male Volunteers", *Digestive Diseases and Sciences,* 1992, 37(1): p. 1576–82.

Vincent, C. A., "A Controlled Trial of the Treatment of Migraine by Acupuncture", *The Clinical Journal of Pain,* 1989, 5(4): p. 305–12.

Yaman, L. Sezai, "The Place of Acupuncture in the Management of Psychogenic Impotence", *Eur Urol,* 1994; 26:52–55.

Werntoft, Elisabet, "Effect of Acupuncture on Nausea and Vomiting During Pregnancy A Randomized, Placebo–Controlled, Pilot Study", *Journal of Reproductive Medicine,* 46(9).

* cited by examiner

DEVICE FOR SURFACE STIMULATION OF ACUPUNCTURE POINTS

CROSS REFERENCE TO RELATED APPLICATION

This application is a continuation-in-part of co-pending International application PCT/US02/08480 filed Mar. 19, 2002, which designated the U.S., claims the benefit of U.S. Provisional Patent application No. 60/277,367 filed in English Mar. 20, 2001, and incorporates the same by reference.

BACKGROUND OF THE INVENTION

The invention relates to a device for stimulating acupuncture points of a body and, more particularly, for stimulating them from the surface of the body with electricity.

Acupuncture is an ancient medical art dating back more than 2000 years. Traditionally, points in the human body (herein called acupuncture points) were reached by piercing the body with fine wires or needles. The needles were then rotated or oscillated about their longitudinal axes, for example by rubbing an exposed end of a needle between a thumb and finger, to stimulate the acupuncture points.

Stimulation of specific acupuncture points has been shown in several studies to have great utility as adjuvant therapy to conventional medical treatments such as nausea and vomiting, postoperative pain, headache, smoking cessation, erectile dysfunction, depression, male fertility, dysmenorrhea, and stomach acid secretion. Great impetus to the use of acupuncture was generated when the National Institutes of Health Consensus Conference on Acupuncture in 1997 showed efficacy of acupuncture in adult postoperative and chemotherapy nausea and vomiting and in postoperative dental pain, and that there were other situations, such as addiction, stroke rehabilitation, headache, menstrual cramps, tennis elbow, fibromyalgia, myofascial pain, osteoarthritis, low back pain, carpal tunnel syndrome, and asthma, in which acupuncture may be useful as an adjunct treatment or an acceptable alternative or be included in a comprehensive management program.

The publications described above and listed below are incorporated herein by reference:

Werntoft,E and Dykes,A, Effect of Acupressure on Nausea and Vomiting During Pregnancy: A Randomized, Placebo-Controlled, Pilot Study. J of Reprod Med, 2001,9:, p835–839

Schlager, A., T. Offer, and I. Baldissera, Laser stimulation of acupuncture point P6 reduces postoperative vomiting in children undergoing strabismus surgery. Br J Anaesth, 1998. 81(4): p. 529–32.

De Aloysio, D. and P. Penacchioni, Morning sickness control in early pregnancy by Neiguan point acupressure. Obstet Gynecol, 1992. 80(5): p. 852–4.

Dundee, J. W., et al., Acupuncture prophylaxis of cancer chemotherapy-induced sickness. J R Soc Med, 1989. 82(5): p. 268–71.

Chen, L., et al., The effect of location of transcutaneous electrical nerve stimulation on postoperative opioid analgesic requirement: acupoint versus nonacupoint stimulation. Anesth Analg, 1998. 87(5): p. 1129–34.

Christensen, P. A., et al., Electroacupuncture and postoperative pain. Br J Anaesth, 1989. 62(3): p. 258–62.

Shen, J et al, Electroacupuncture for Control of Myeloablative Chemotherapy Induced Emesis: A Randomized Controlled Trial, JAMA, 2000, 284(21): p. 2755–2761

Vincent, C. A., A controlled trial of the treatment of migraine by acupuncture. Clin J Pain, 1989. 5(4): p. 305–12.

Waite, N. R. and J. B. Clough, A single-blind, placebo-controlled trial of a simple acupuncture treatment in the cessation of smoking. Br J Gen Pract, 1998. 48(433): p. 1487–90.

Kho, H. G., et al., The use of acupuncture in the treatment of erectile dysfunction. Int J Impot Res, 1999. 11(1): p. 41–6.

Luo, H., et al., Clinical research on the therapeutic effect of the electro-acupuncture treatment in patients with depression. Psychiatry Clin Neurosci, 1998. 52 Suppl: p. S338–40.

Siterman, S., et al., Effect of acupuncture on sperm parameters of males suffering from subfertility related to low sperm quality. Arch Androl, 1997. 39(2): p. 155–61.

Helms, J. M., Acupuncture for the management of primary dysmenorrhea. Obstet Gynecol, 1987. 69(1): p. 51–6.

Tougas, G., et al., Effect of acupuncture on gastric acid secretion in healthy male volunteers. Dig Dis Sci, 1992. 37(10): p. 1576–82.

NIH Consensus Conference. Acupuncture JAMA, 1998. 280(17): p. 1518–24.

Omura, Y., Simple custom-made disposable surface electrode system for non-invasive "electro-acupuncture" or TNS and its clinical applications including treatment of cephalic hypertension and hypotension syndromes as well as temporo-mandibular joint problems, tintinitus, shoulder and lower back pain, etc. Acupunct Electrother Res, 1981. 6(2–3): p. 109–34.

However, many patients resist acupuncture primarily due to a fear of its needling or a contraindication for acupuncture using acupuncture needles (e.g., bleeding disorders, active infection). The needle phobic pediatric patient, in particular, is extremely reluctant. Therefore, electric stimulation of acupuncture points from the skin or surface of a body without invasive needles has been tried. The following patents on electric stimulation inside a human body from the skin or surface of the body at least acupuncture-like without needles and considered to be the references most pertinent to my invention are also incorporated herein by reference.

Kitov U.S. Pat. No. 4,915,110, issued Apr. 10, 1990 describes a device consisting of a center and outer circular electrically conducting material covered by a current insulating material.

The device includes:

1. concentric electrodes with an electrically insulating covering on the outer (annular) electrode.

2. A method for inducing an electrostatic charge between the two electrodes for field stimulation of an acupuncture point.

The device does not include:

1. A self-adhering, electrically conductive device which is flexible and can be positioned anywhere on the body.

2. Surface electrical stimulation to a specific acupuncture point.

Frick U.S. Pat. No. 4,907,601 issued Mar. 13, 1990 describes a device consisting of center electrode surrounded by outer electrodes comprised of gold or gold alloy. Each of the outer electrodes supplied power independently by a switching device with the center electrode being the reference pole.

The device includes:

1. concentric electrodes 2. gold or gold alloy electrodes

3. A switching device that switches between one of the outer electrodes and center electrode in a programmed fashion. In the range of frequencies between 0,5 and 20 Hz.

4. Outer and inner electrodes are of different surface measurements.

The device does not include:

1. A self-adhering device which can be positioned anywhere on the body.

2. A electrically conductive gel or electrically conductive gel/adhesive coupling to Silver/Silver chloride electrode surfaces.

3. A electrically non-conductive adhesive surrounding electrically conductive gel wells to allow for attachment of the device to the skin.

4. A self-contained electrical conductive gel/adhesive to couple the electrical signal between the electrode and the skin surface.

5. An outer annular array functioning as a single electrode in relationship to the center electrode operating between 1 and 500 Hz.

Axelgaard U.S. Pat. No. 5,785,040 (also U.S. Pat. No. 5,450,845) issued Jul. 28, 1998 describes a device consisting of an electrically non-conducting backing material, a flexible electrically conductive patch, a lead wire connected to the electrically conductive portion and a separate gel pad for releasably coupling to the surface of the skin. The gel pad being able to include a drug for iontophoretic delivery.

The device includes:

1) A flexible electrode patch with an attached wire lead and conductive gel pad.

2) A method for providing an array of these electrode patches on a single flexible sheet (backing) which provides compression by use of stretchable straps for electrical stimulation between them.

The device does not include:

1) a self-adhering device which can be positioned anywhere on the body.

2) concentric electrodes; and 3) provisions for variable frequencies and pulse widths as required for the specific acupuncture point to be stimulated.

Wilson U.S. Pat. No. 4,398,545, issued on Aug. 16, 1983, illustrates a bandage type device designed to block pain impulses originating from an injury.

From its Abstract:

A bandage to be applied adjacent to an injured portion of a patient's body contains electronic circuitry which delivers electric pulses into the body to block or mask the pain arising from the injury. The bandage includes an inner unit adapted to be applied directly onto the patient's skin and a removable outer unit adapted to be applied upon the inner unit. The inner unit includes spaced apart conductive portions which contact the patient's skin. The outer unit includes a power source and an electronic circuit which applies a voltage output to the conductive portions of the inner unit. The voltage output is transmitted through the conductive portions to the patient's skin to cause low current electrical pulses within the patient's body to block or mask the pain arising from the injury.

The device includes:

1) an inner and outer unit, the inner unit including two flat electrodes with opening for electrolyte (conductive) solution and the outer unit containing electronic circuitry; and 2) two large electrodes patches which are used for skin contact and to direct current flow.

The device does not include:

1) an indication or application for stimulation of acupuncture points; it is designed to be used for muscular pain and is applied directly to the affected area; and 2) concentric electrodes about a center electrode and an outer circumferential electrode, both electrodes using an electrolytic gel, which allows a low resistance connection between the electrode and the skin.

The Bertolluci U.S. Pat. No. 4,981,146 issued on Jan. 1, 1991, illustrates a watch like device designed to alleviate nausea. From its Abstract:

A nausea control device is provided in the form of a watch-like housing and related attachment band for mounting onto the human wrist, wherein the device includes electronic circuitry for imparting electrical impulses via positive and negative electrodes to the pericardium six (P6 a.k.a. MH6) acupuncture point for alleviating nausea. Batteries within the housing power the electric circuitry, and a manually operable switch on the housing controls on/off and pulse amplitude.

The device includes:

1) an inner and outer unit, the inner unit including linear arranged electrodes for a specified frequency (70 Hz) and pulse width (80 ns) and the outer unit containing electronic circuitry;

2) surface stimulation of an acupuncture point; and 3) variable amplitude adjustment.

The device does not include:

1) a self-adhering device which can be positioned anywhere on the body, including many other acupuncture points in addition to MH6.

2) concentric electrodes; and 3) provisions for variable frequencies and pulse widths as required for the specific acupuncture point to be stimulated.

The references cited in the Bertolluci patent include:

the Hoffman U.S. Pat. No. 3,107,672, and the Moss U.S. Pat. No. 3,424,165, which are directed toward stimulating and firming the muscles for cosmetic purposes;

the Oseau U.S. Pat. No. 3,911,910, which teaches devices designed to relieve involuntary muscle spasticity;

the Crossley U.S. Pat. No. 4,715,367, which teaches devices to assist in refraining from undesirable habits by utilizing painful or alarming electrical stimulation; and the Hathaway U.S. Pat. No. 2,223,447, which illustrates a non-portable radiotherapy system designed for treatment of certain diseases.

None of these are designed for use specific to acupuncture points, none use a concentric arrangement of outer and inner electrode and none are able to be used without assistance.

However, the Omura publication incorporated above describes a disposable flat surface electrode to be constructed by the practitioner out of adhesive tape, aluminum foil and thumb tacks for use in electro-acupuncture. It is similar to the Wilson U.S. Pat. No. 4,398,545 in design and application and, therefore, has the same differences from my invention.

Grey U.S. Pat. No. 6,272,383, which extends the Bertolluci patent 'wrist band' type device to two points on the calf (GB-39 and ST-36).

The device does not include:

1) a self-adhering device which can be positioned anywhere on the body, including many other acupuncture points.

2) concentric electrodes; and 3) provisions for variable frequencies and pulse widths as required for the specific acupuncture point to be stimulated.

Garcia-Rill U.S. Pat. No. 5,950,635 relates to treatment of an anxiety disorder with stimulation of 3 acupuncture points (LR-3, HT-3, PC-6) with either acupuncture needles or standard TENS electrodes at a specified frequency (5 Hz).

The device does not include:

1) a self-adhering device which can be positioned anywhere on the body.

2) concentric electrodes; and 3) provisions for variable frequencies and pulse widths as required for the specific acupuncture point to be stimulated.

Cazaux U.S. Pat. No. 5,957,951 relates to a []wrist-watch[] type device with multiple contact points arranged in a linear array of three rows and three columns connected to a stimulator (pulse generator) which provides stimulation to one or more points on the wrist underlying the contact points to treat various conditions.

The device does not include:

1) a self-adhering device which can be positioned anywhere on the body, including many other acupuncture points.

2) concentric electrodes.

SUMMARY OF THE INVENTION

My device provides a non-invasive means for stimulating a selected acupuncture point. It can be used to stimulate almost any acupuncture points. Through use of its novel electrode configuration, electrical impulses are delivered to the selected acupuncture point with limited current loss, thus lowering the power requirements of the device. The electrode configuration also provides for easy measurement of a body dimension unit termed a cun (defined as the length of the middle phalangeal bone of the middle finger) that is used in acupuncture procedures. The low power requirements will allow for a small self-contained power and/or control unit (e.g., a stimulator) to be attached []piggyback" to the electrode as well as use of a standard external power supply or entire stimulator.

Although many of these devices can be used together at separate acupuncture points for what is often referred to as an energetic treatment, a major intent of this device is stimulation of one acupuncture point at a time.

The device, which is preferably disc shaped, has two primary electrically insulative layers. A first layer has one side, which is the lower side in use, for adhering to, e.g., a patient's skin surface, a second, upper layer on the underside of which electrical circuitry is preferably printed so that the electrical circuitry is sandwiched between the layers. The device can be made in several sizes to accommodate patient size and location of the acupuncture point to be stimulated. Two distinct forms of the device are presented: a single use device useful for treatments requiring a single application of the device and a reusable device for treatments requiring repetitive applications of the device in a single patient. In the single use device, the first, lower layer is preferably a foam with non-conductive adhesive on both sides: the bottom side for adhering to the skin and the top side for adhering to the upper polyester disc. The holes through this lower foam layer include, preferably, eight holes spaced concentrically about one central hole in the middle of the lower foam layer. All these holes are, preferably, overfilled with an electrically conductive gel that projects from the lower foam layer. The conductive circuitry preferably printed on the underside of the upper layer provides a series connection to the gel in each of the eight concentric holes and a separate connection to the gel in the center hole when the upper layer is adhered to the lower layer. The printed circuitry may be a silver/silver chloride polymer film, also provides for a tab(s) which can be permanently or temporarily affixed to an integral or remote simulator through direct contact or wire leads. In the reusable device a pressure-sensitive electrically conductive adhesive material forms the lower layer which allows for multiple applications to a patient's skin. The adhesive lower layer is transparent to show the cun spacing of a circular central electrode the annular electrode being a continuous circle in this embodiment. The electrodes are preferably silver/silver chloride polymer film. Metal core insulated leads can be use for electrical connection to the silver/silver chloride polymer film. The opposite ends of the leads are connected to jacks for connection to an impulse stimulator. The layers and electrode films are manually flexible.

At least several of the forms of the electrode disc may be received on the base of a power and/or control unit for holding the unit thereon, whereby the electrode disc can be adhered at an acupuncture point on a body and the power and/or control unit mounted thereon for providing a self-contained acupuncture treatment thereto.

Examples of several acupuncture points for which this device is applicable include (but not limited to):

MH6 (Nei Guan):

Location: On the anterior antebrachial region, 2 cun proximal to the anterior crease of the wrist, on the ulnar side of the tendon of the flexor carpi radialis, between this tendon and the tendon of the palmaris longus (when it exists);

Indications: Important for mental-emotional symptoms, asthma, gastritis, nausea, motion sickness, hiccoughs, heartburn, or tennis elbow;

Frequency: 2.5 Hz to 100 Hz;

CV-12 (Zhon Guan):

Location: On the anterior midline, 4 cun above the umbilicus, midway between the umbilicus and the xiphisternal synchondrosis;

Indications: Stomach pain, vomiting, gastritis, stomach or duodenal ulcers, abdominal distension, diarrhea, anorexia, dysentery, malnutrition, loss of appetite, belching, or retention of food in stomach;

Frequency: 2.5 Hz to 100 Hz;

LI-4 (He Gu):

Location: On the dorsum of the first interosseus space of the hand, at the level of the midpoint of the shaft of the 2nd metacarpal bone, on the belly of the first interosseus dorsalis muscle;

Indications: headaches, sinus problems, toothaches, mouth and tooth disorders, urticaria and skin problems, tonsillitis, pharyngitis, epistaxis, rhinitis, sinusitis, nose diseases, nosebleed, conjunctivitis and eye problems, facial paralysis, tintinitus, hearing loss, diarrhea, constipation, insomnia, emotional agitation, or depression;

Frequency: 2.5 Hz to 100 Hz;

TH-5 (Wai Guan):

Location: On the posterior antebrachial region, 2 cun proximal to the dorsal crease of the wrist, on the line connecting TH-4 and the tip of the olecranon;

Indications: stiffness in elbow, forearm and wrist, shoulder problems. occipital headaches, migrating to forehead and eyes, tintinitus, ENT problems, deafness, otitis, abdominal pain, constipation or tennis elbow;

Frequency: 2.5 Hz to 100 Hz;

SP-6 (San Yin Jiao):

Location: On the medial side of the leg, posterior to the medial margin of the tibia, 3 cun above the prominence of the medial malleolus;

Indications: immune and endocrine stimulation, reproductive problems, dysmenorrhea, leukorrhea, orchitis, hernia, spermatorrhea, urinary problems (incontinence or obstruction), lower abdominal pain, diarrhea and abdominal distension, or borborygmus;

Frequency: 2.5 Hz to 500 Hz;

LR-3 (Tai Chong):

Location: On the dorsum of the foot, on the first interosseus space of the metatarsus, in a depression distal to the intermetatarsal joint between the 1st and 2nd metatarsal bones;

Indications: anxiety, insomnia, all foot problems, liver or gall bladder disease, abdominal pain and swelling, nausea and vomiting, all eye problems, nasal congestion due to allergies, allergic headaches, particularly ocular or at top of head, myopia, glaucoma, and visual disorders, insomnia, migrane headaches, irritability, dizziness, seizures in children, sore throat, menstrual disorders, slow labor, genital pain, testicular pain and swelling, hernia pain, thoracic fullness, abdominal pain, diarrhea, enuresis, urinary block, or endocrine and metabolic disorders;

Frequency: 2.5 Hz to 100 Hz;

ST-36 (Zu San Li):

Location: On the superolateral aspect of the anterior surface of the leg, 3 cun distal to the apex of the patella and one finger-breadth lateral to the tibial tuberosity;

Indications: abdominal pain, appendicitis, nausea and vomiting, gastritis, pain, diarrhea, constipation, dyspepsia, gastric ulcer. hepatitis and cholecystitis. all pain problems, fatigue, dizziness, convulsions, needle shock, asthma and respiratory problems, weight loss, febrile diseases, arterial hypertension, hemiplegia, edema, or epilepsy;

Frequency: 2.5 Hz to 500 Hz; and

ST-43 (Xian Gu):

Location: On the dorsum of the foot, on the 2nd interosseus space of the metatarsus, in a depression distal to the intermetatarsal joint between the 2nd and 3rd metatarsal bones;

Indications: agitation, insomnia, nightmares, night sweats, fever, or redness of face or eyes;

Frequency: 2.5 Hz to 100 Hz.

BRIEF DESCRIPTION OF THE DRAWING

The above and other features of the invention will now be described with reference to a drawing of embodiments that illustrate but do not limit the invention and in which.

DESCRIPTION OF THE INVENTION

Figure 1:
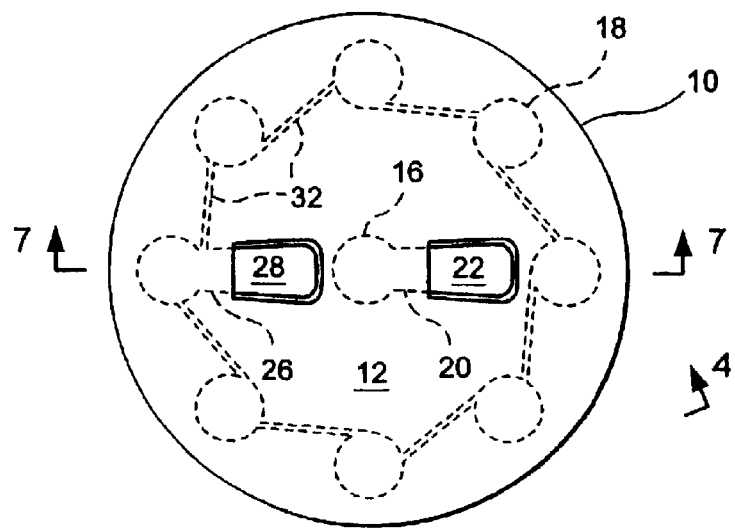
FIG. 1 is a top plan view of a first embodiment of the device in a shipping condition.

Each preferred embodiment of the device has an electrode disc 10, 10a, 10b or 120 shown by itself in FIGS. 1–7, 13.

In the single use configuration the electrode disc has an electrically insulating disc-shaped transparent polyester layer 12, 12a, 12b about 3–7 mil thick on one surface that is the top in use. The underside at least of the polyester layer may be adhesion treated. A congruent, electrically insulating polyethylene foam disc with skin contact pressure sensitive adhesive on both sides forms a lower layer 14, 14a, 14b of each embodiment. The adhesive on one side adheres to the polyester layer 12, 12a, 12b and the adhesive on the opposite surface that is on the bottom in use contacts and removably adheres to a patient's skin. The polyethylene foam may be about 32 mil thick with an adhesive tack in gm/sq cm of about 400 on both sides. In another embodiment (not shown) the layers are not congruent and/or disc shaped.

An electrically conductive gel 16, 16a, 16b overfills a central hole through the adhesive foam layer to project from the lowermost (in use), skin-contacting surface thereof. Further gel 18, 18a, 18b overfills a series of further holes (eight in the drawn embodiments) through the adhesive foam layer spaced about a circle centered on the hole for the central gel 16, 16a, 16b. A suitable gel comprises a conductive hydrogel polymer as for example provided for skin contact devices by First Water Limited of Ramsbury, Marlborough, U.K.

Figure 2:
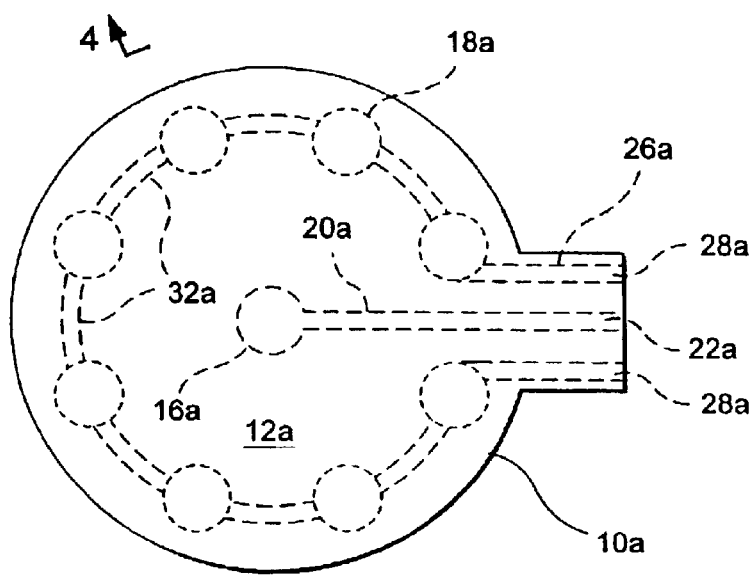
FIG. 2 is a top plan view of a second embodiment of the device.
Figure 3:
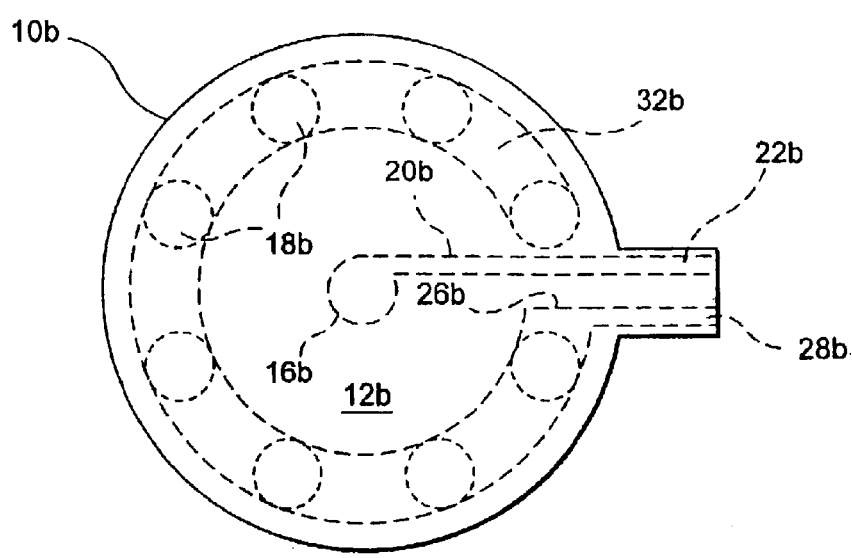
FIG. 3 is a top plan view of a third embodiment of the device.
Figure 4:
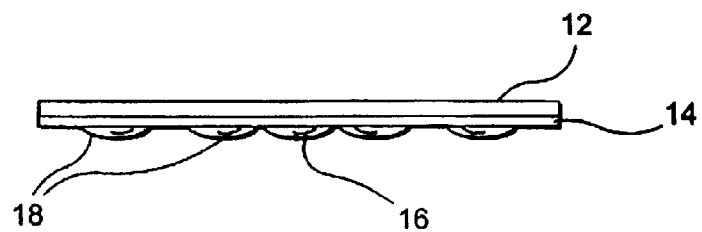
FIG. 4 is a front and sides elevational view of the first embodiment of the device in the shipping condition, the rear and sides elevational view being a mirror image and, therefore, not shown.
Figure 5:
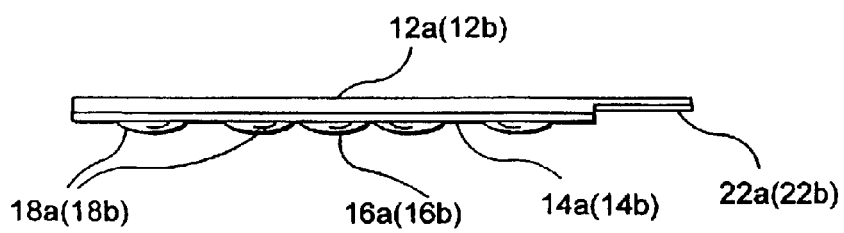
FIG. 5 is a front and sides elevational view of the second and third embodiments, the rear and sides elevational view being a mirror image and, therefore, not shown.
Figure 6:
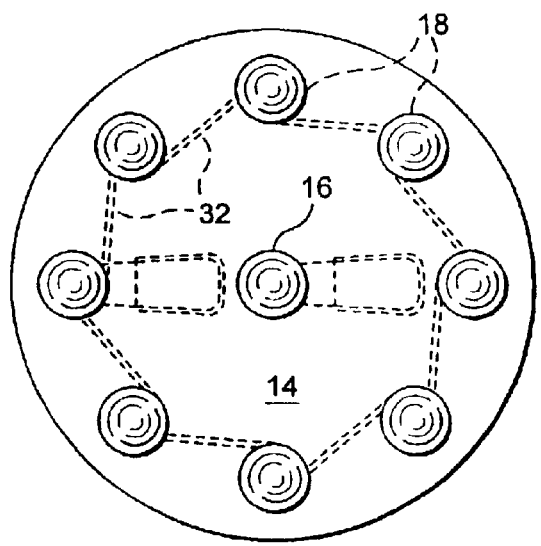
FIG. 6 is a bottom plan view of the first embodiment of the device in the shipping condition.

The central gel filled hole 16, 16a, 16b is connected to one end of a silver/silver chloride polymer film electrical conductor 20, 20a, 20b that is printed on the underside of the polyester layer 12, 12a, 12b to be sandwiched between the polyester layer and the adhesive foam layer 14, 14a, 14b. The conductor 20, 20a, 20b projects radially from the one end connected to the central gel-filled hole to an opposite, tab end 22, 22a, 22b. In the first embodiment, the plastic layer is cut away over the tab end, whereby the tab end can be raised from a layer-parallel shipping condition shown in FIGS. 1, 6 and 7 to a projecting use condition shown in FIGS. 7, 8 and 10 by a folding movement indicated by the arrow 24 in FIG. 7. In the second and third embodiments, the top polyester layer 12a, 12b projects radially from the disc in tabs to support the silver/silver chloride polymer film electrical conductor tab ends 22a, 22b printed on the undersurface of the tabs of the polyester layers 12a, 12b as shown in FIG. 2, 3 and 5.

One end of another, similar silver/silver chloride conductor 26, 26a, 26b is connected to one of the further gel filled holes 18, 18a, 18b and projects radially to a separate tab end 28, 28a, 28b. In the first embodiment, the polyester layer 12 is cut away over the tab end 28 so that it, too, may be folded as shown by arrow 30 in FIG. 7 from a layer-parallel shipping condition to a projecting, use condition. In the second and third embodiments, the tab ends 28a, 28b are supported by the tabs of the polyester layer in spaced parallel relation to the tab ends 22a, 22b of the conductors from the central gel filled holes.

The further gel filled holes 18, 18a, 18b are also connected to each other by silver/silver chloride polymer film conductors 32, 32a, 32b printed on the polyester layer between and over the holes and sandwiched between the layers.

In the first embodiment, the conductor 32 extends diagonally from a radially inward portion of one gel filled hole 18 to a radially outward portion of a successive gel filled hole 18 about the circular spacing there between and over each gel filled hole. This diagonal arrangement between the gel filled holes and the circular arrangement of the gel filled holes define at about longitudinal centers of the gel filled holes 18 an effective circle that is an integral multiple (including of 1) of an average cun radially from the central gel filled hole 16. In this way, the device provides a visual cun-measuring tool for positioning it in cun dimensions relative to an acupuncture point.

In the second embodiment, the conductor 32a extends from the one end of the conductor 26a connected to one gel filled holes 18a across and over each of the gel filled holes 18a to an opposite end on the tab of the polyester layer. Since the resulting circle of the conductor 32a is narrower than the diameters of the holes, a cun-indicating circle from the central gel filled hole is clearly defined and since both opposite sides of the tab of the polyester layer effectively have a tab end 28a of the conductor, the device is adapted for right- or left-handed electrical connection to the circle of gel filled holes with the central hole being visually conspicuously connected to a tab end 22a in the middle. Therefore, the tab ends 22a, 28a cannot be confused if, for example, relative positive and negative connections thereto are desired.

In the third embodiment, the circle of the conductor 32b is wide enough to cover the gel filled holes. Circumferential alignment between portions of the conductor and the gel filled holes is, therefore, not needed. Also, only the tab end 28b of the connected conductor 26b extends onto the tab of the polyester layer.

Figure 7:
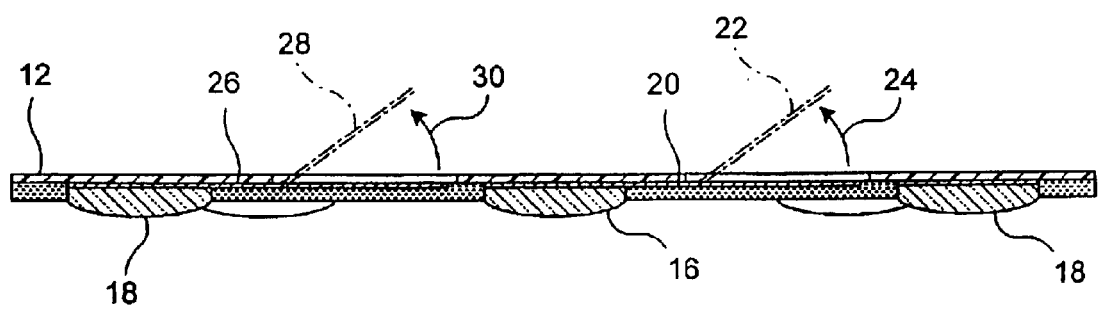
FIG. 7 is an enlarged sectional elevational view of the first embodiment of the device line 7—7 in FIG. 1 in the shipping condition and showing in phantom tabs being raised into a use condition.
Figure 8:
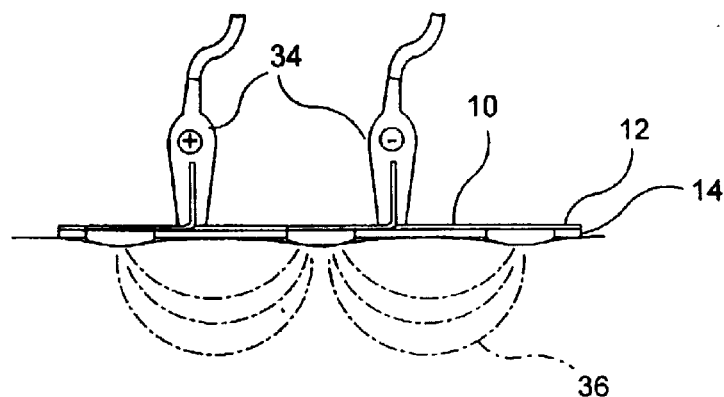
FIG. 8 is a front and sides elevational view of the first embodiment of the device in a use condition together with electrode clamps and wire leads therefor, the rear and sides elevational view being a mirror image and, therefore, not shown.
Figure 9:
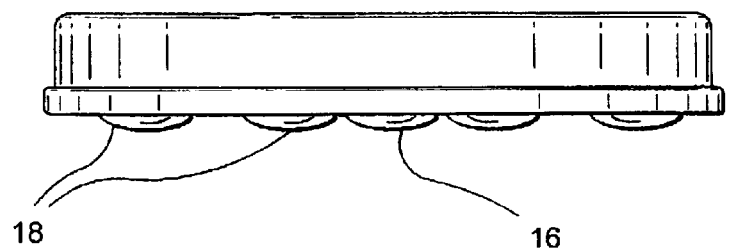
FIG. 9 is a front and sides elevational view of the first embodiment of the device in the use condition together with a complementary power and/or control unit therefor.

When the device is adhered on a patient's skin over an acupuncture point, the tabs 22, 28 of the first embodiment can be raised from the layer-parallel shipping condition to a projecting, use condition that is vertical (perpendicular to the disc) as shown in FIG. 8 but could be at other projecting use angles in other embodiments (not shown), as suggested in FIG. 7. In the use condition, the tabs can be engaged by electric supply clamps 34 and wire leads of a known stimulator (not shown) to provide electric pulses for a pulsed electric field 36 as shown in FIG. 8 that stimulates an acupuncture point in the electric-field-penetrated patient's body (not shown) below the device. Similar clamps and wire leads (not shown) may engage the tab ends 22a, 22b, 28a, 28b of the second and third embodiments.

Preferably, however, the tabs 22, 28 of the first embodiment in the perpendicular raised, use condition shown in FIG. 8 slip between electric contacts 38 in slots 39 (FIG. 12) in a power and/or control unit 40 shown in FIGS. 9–12. For this, the power and/or control unit of the device has a base 42 the same diameter as the disc 10 with a lip 44 about it that is the same or slightly less deep as the disc is thick, whereby the adhesive foam layer 14 can adhere the electrode disc 10 to a patient's skin as described above while the lip and tabs hold the power and/or control unit on the adhered disc.

Figure 11:
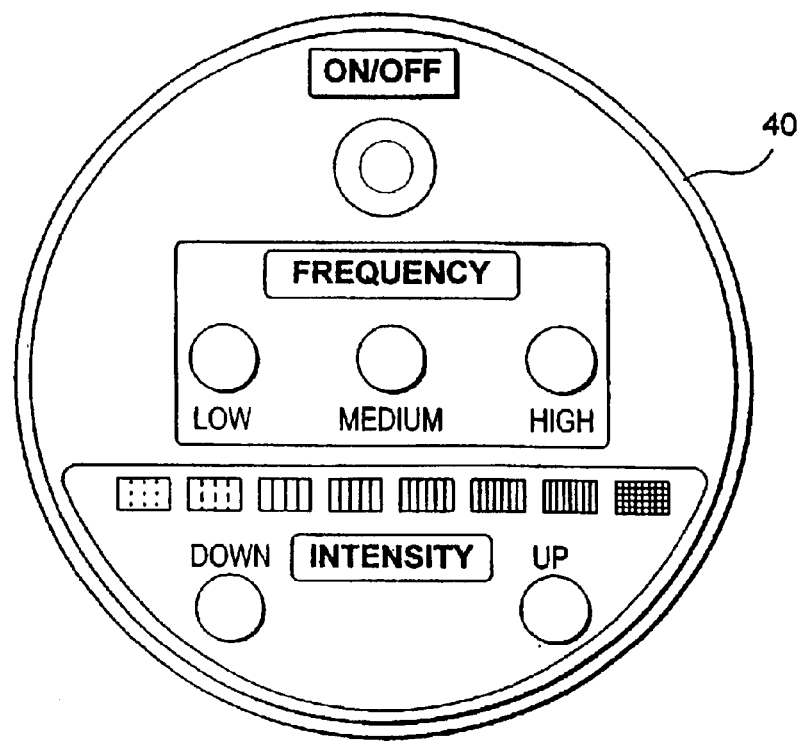
FIG. 11 is a top plan view of the power and/or control unit.

As shown in FIG. 11, the power and/or control unit 40 has on a surface opposite the base a variety of on/off, frequency, pulse width, intensity and/or like controls known for known stimulators.

Figure 12:
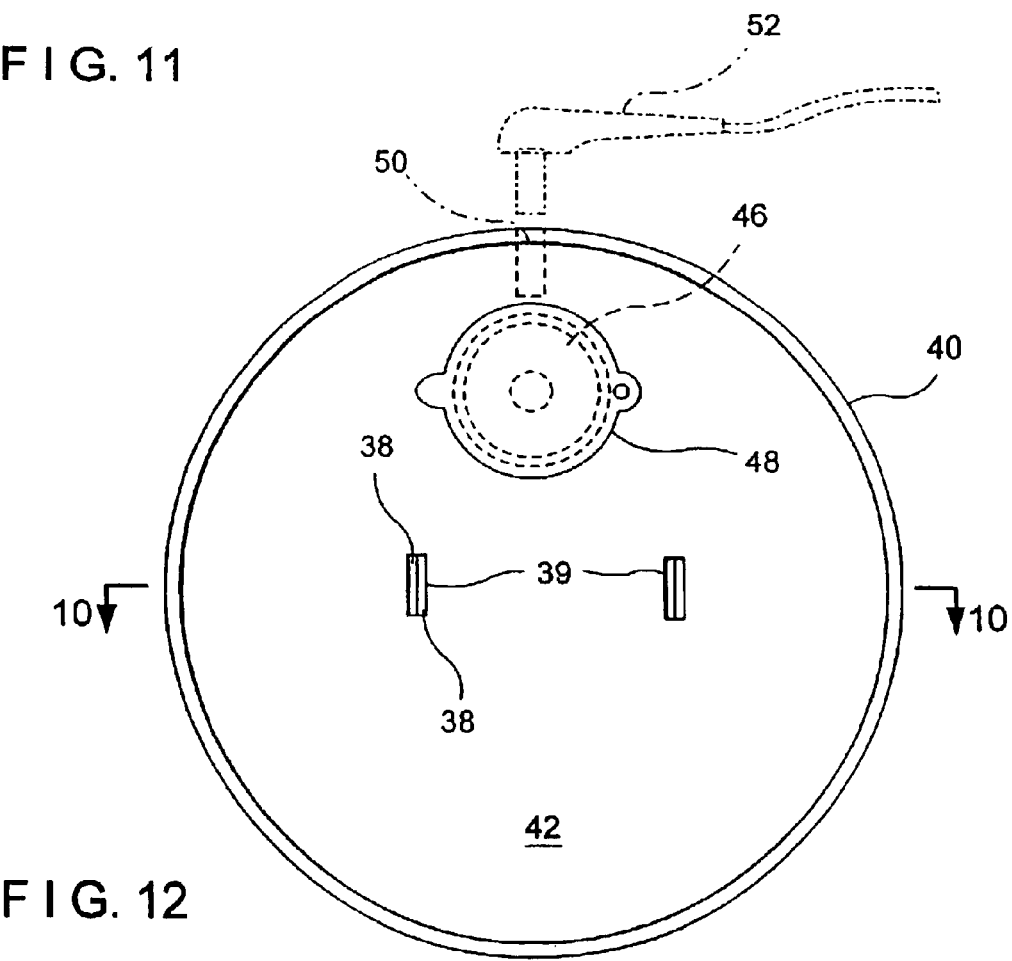
FIG. 12 is a bottom plan view of the power and/or control unit without the first embodiment of the device.
Figure 13:
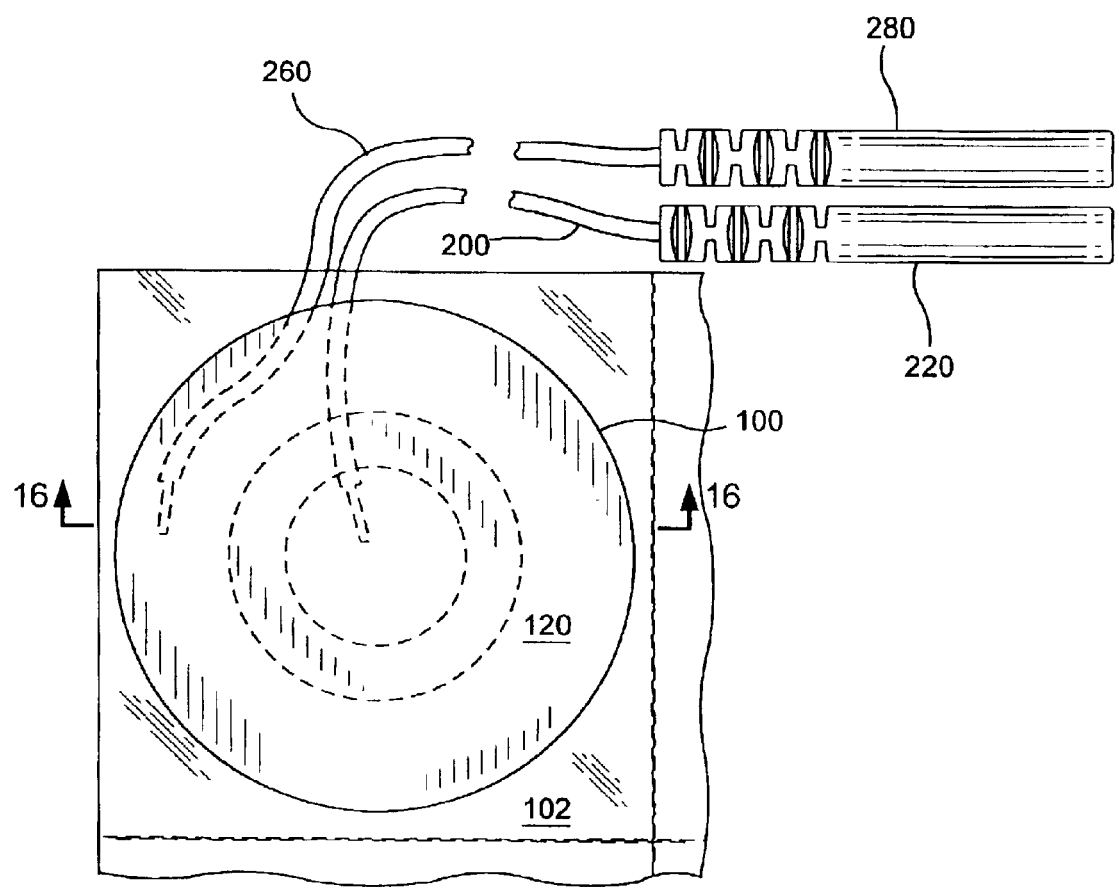
FIG. 13 is an enlarged top plan view, partly cut away, of a fourth embodiment of the device in a shipping condition.
Figure 14:
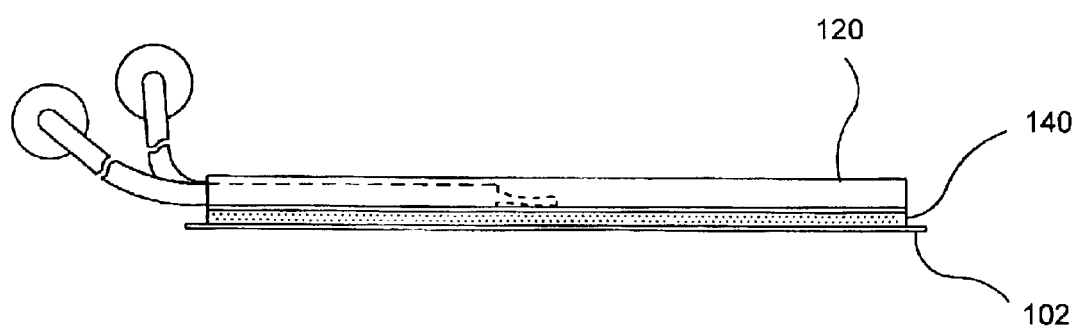
FIG. 14 is a left side elevational view thereof.
Figure 15:
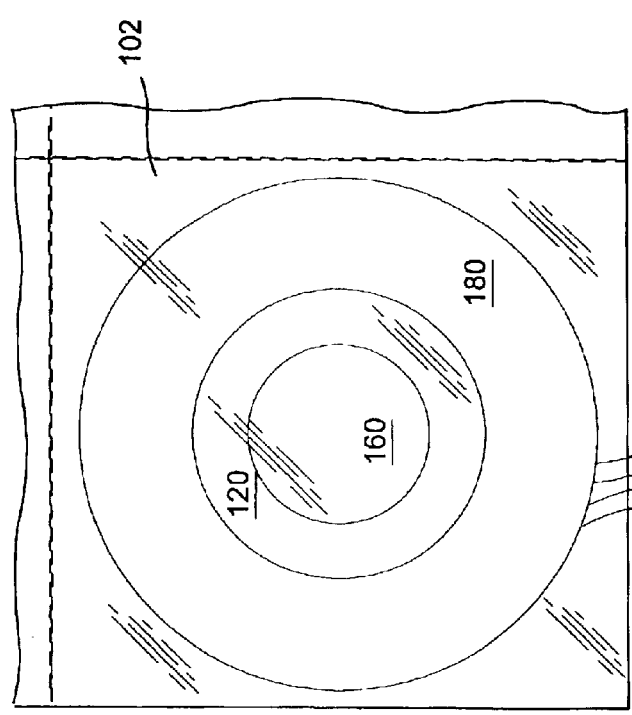
FIG. 15 is a bottom plan view thereof.

As shown in FIG. 12, the power and/or control unit 40 includes a battery 46 for power. The battery is accessible through a battery hatch cover 48 in the base 42 of the power and/or control unit.

Figure 10:
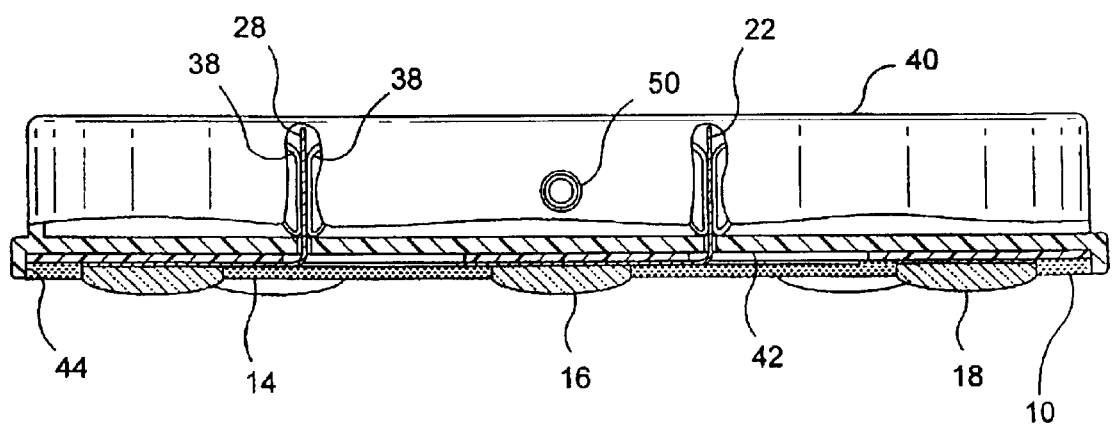
FIG. 10 is an enlarged rear elevational view, partly cut away and partly in section, of the first embodiment of the device in the use condition with the power and/or control unit.

However, as shown in FIGS. 10 and 12, the power and/or control unit also has a port 50 in its rear elevation of receiving a power jack 52 that can supply power in place of or in addition to the battery. Other embodiments (not shown) may have only one or the other of the battery 46 or port 50 for power.

As thus descried, a self-contained, self-adhesive device is attached to electronic circuitry either directly as in FIG. 10 or through wire leads as in FIG. 8 to provide electrical impulses to a specific acupuncture point under the patient's skin. The disc has a fixed central gel electrode with an outer circular gel electrode arrangement spaced from the central gel in cun units to assist in location at the acupuncture point.

The foam layer also provides in this case elasticity to assure adequate pressure the central gel electrode with the patient's skin at the acupuncture point while the adhesive secures the rest of the disc to the skin for providing a low resistance circuit with the acupuncture point.

This electrode complex is attached to an impulse stimulator consisting of a power source and electronic circuitry with controls for impulse intensity and frequency. The electronic impulse stimulator allows for a stimulation frequency between about 2 Hz and 500 Hz, a pulse width between about 40 μs and 260 μs, and a pulse amplitude between about 1 mill ampere and 50 mill amperes. It is designed to attach directly to the electrode disc at least in the first embodiment of FIG. 1.

The disc is applied to the skin over a specific acupuncture point. The distance between the center and outer circular gel electrodes is designed to provide a convenient ruler for proper placement of the device. The diameter of the disc used will be determine by the patient size and acupuncture point to be stimulated. A single unit can be used alone to provide a therapeutic effect or a combination of several units can be employed for what is often referred to as an energetic therapeutic approach. When in place, the device is activated at the specified frequency as described above. The current is then increased until the pulsation is at an intensity level comfortable for the patient.

The fourth embodiment (reusable configuration) of the electrode disc 100 shown in FIGS. 13 to 16. The top layer 120 in such use is opaque in the fourth embodiment. Therefore, the adhesive lower layer 140 are preferably transparent to show the cun spacing of a circular central electrode 160 and an annular electrode 180 thereabout, the annular electrode being a continuous circle in this embodiment. For such showing, the electrodes preferably contrast visually with the top layer, the transparency of the second layer being relative to the contrast of the electrodes so that the electrodes can be seen through the second layer. The electrodes are preferably silver/silver chloride polymer film. The layers 120, 140 are congruent discs.

Metal core insulated leads 200, 260 are stripped at ends that penetrate between the top layer 120 and the electrodes 160, 180, respectively, for electrical connection thereto. Opposite ends of the leads are connected to jacks 220, 280, respectively, for connection to an impulse stimulator (not shown) as in the previously described embodiments. In other embodiments, the leads and jacks could be replaced by films and tabs like the silver/silver-chloride polymer film leads 20, 20*a*, 20*b*; 26, 26*a*, 26*b* and/or tabs 22, 22*a*, 22*b*; 28, 28*a*, 28*b* shown in FIGS. 1–3.

Figure 16:
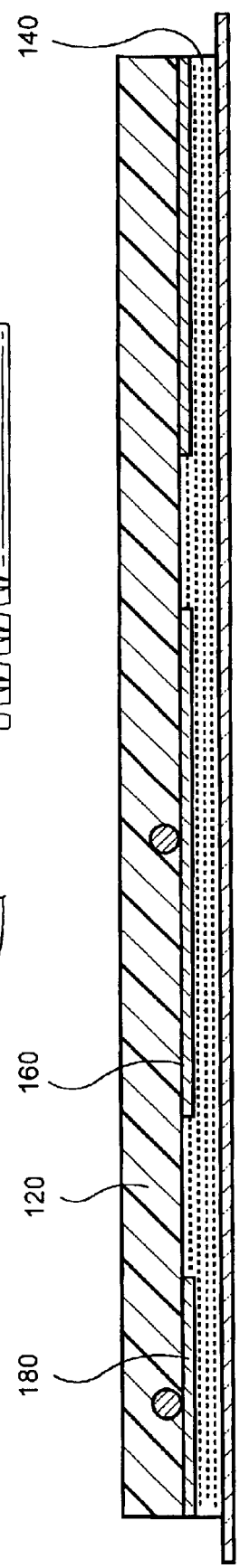
FIG. 16 is a partly broken away further enlarged sectional view on line 16—16 of FIG. 13.

As best appreciated from FIG. 16, the adhesive lower layer 140 extends between the electrodes 160, 180 and, transversely, between the electrodes 160, 180 and the patient's skin for use. Therefore, in addition to the transparency already described as preferred, the adhesive lower layer also has a conductivity (resistivity) sufficient to connect to the patient's skin but insufficient to short between the electrodes.

It is further preferred that the adhesive lower layer 140 retain its adhesive qualities after removal from one place on a patient's skin so as to be able to adhere to another place on a patient's skin so that successive acupuncture points can be stimulated without having to replace the disc 100 each time. This saves time in not having to reconnect a new disc to a stimulator and, of course, saves cost in not having to replace so many discs.

These and other characteristics of the adhesive lower layer 140 may be found in, for example, AmGel 600 and AmGel 700 multistick stimulating series gels made by AmGel Technologies of Fallbrook, Calif. These gels are each further described in a corresponding Material Safety Data Sheet thereof of Aug. 1, 2002 and Mar. 25, 2002, which are incorporated by reference.

A particularly preferred combination of the above features has the layers 120, 140 and electrodes 160, 180 manually flexible for ease of application and removal and to conform to the topography at the desired acupuncture point initially and during movement, whether voluntarily or involuntarily by bumping or breathing, for example, while retaining the desired electrical communication with the skin. In combination with the adhesive property, this broadens the locations for use and makes such use easier in application to points where the patient's skin has at least a component in a vertical direction, for example, as rigid, non-adhesive electrodes could not.

Other particular features thus are:

self contained, self adhesive device providing single non-invasive acupuncture point stimulation;

elasticity of electrode disc material that provides for proper pressure of the center electrode at the acupuncture point for a low resistance pathway;

circular outer electrode pattern around a central electrode to produce a uniform current field that minimizes loss as well as providing for latitude in placement of the electrode disc;

a concentric electrode arrangement that assures proper orientation of the electromagnetic field;

the distance between the center electrode and outer circumferential electrode (which varies with the physical size of the electrode disc) is a "cun" (a term referring to a body unit which is the units used to measure the precise location of the acupuncture point from specific anatomical landmarks) to incorporate a ruler for locating the specific location of the acupuncture point of interest, which may be on the trunk or extremities of the patient's body; and application for needle phobic and pediatric population.

These and other features in equivalence, combination or permutation as may occur to those of ordinary skill in the art are contemplated as within the scope of the following claims.

What is claimed is:

1. In a device for surface stimulation of an acupuncture point, the improvements comprising:

a first electrically insulating layer;

a pressure sensitive, electrically insulating adhesive second layer having one side adhered on one surface of the first layer, whereby an opposite side of the second layer adheres to a skin surface for use, the second layer having a central hole and a series of holes spaced about a circle about the central hole therethrough;

electrically conductive gel in the holes and projecting therefrom for electrical connection to the skin surface when the opposite side of the second layer is adhered thereto;

a first electrical conductor sandwiched between the layers and electrically connecting the gel in the series of holes about the circle;

a second electrical conductor sandwiched between the layers, electrically connected to the gel in the central hole at one end and extending to an opposite, tab end for electrical connection to a stimulator; and a third electrical conductor sandwiched between the layers, electrically connected to the first conductor at one end and extending to an opposite tab end for electrical connection to the stimulator.

2. The device for surface stimulation of an acupuncture point according to claim 1, wherein the first layer has first and second holes therethrough respectively over the tab ends of the second and third conductors for bending the second and third conductors from a shipping condition at least substantially parallel to the first layer to a use condition projecting therefrom.

3. The device for surface stimulation of an acupuncture point according to claim 2, wherein the holes about the circle are radially spaced from the central hole an integral multiple of an average cun.

4. The device for surface stimulation of an acupuncture point according to claim 3, and further comprising a stimulator, wherein the stimulator comprises:

a power and/or control unit having a base for receiving the first layer, the base having slots for receiving the tab ends in the use condition; and contacts in the slots for providing electric power from the contacts to the tab ends.

5. The disc device for surface stimulation of an acupuncture point according to claim 4, and further comprising:

a lip on the base about at least the first layer.

6. The device for surface stimulation of an acupuncture point according to claim 2, wherein the layers are congruent discs.

7. The device for surface stimulation of an acupuncture point according to claim 6, and further comprising a stimulator, wherein the stimulator comprises:

a power and/or control unit having a base for receiving the first layer, the base having slots for receiving the tab ends in the use condition; and contacts in the slots for providing electric power from the contacts to the tab ends.

8. The device for surface stimulation of an acupuncture point according to claim 7, and further comprising:
a lip on the base about the layers.

9. The device for surface stimulation of an acupuncture point according to claim 2, and further comprising a stimulator, wherein the stimulator comprises:
a power and/or control unit having a base for receiving the first layer, the base having slots for receiving the tab ends in the use condition; and
contacts in the slots for providing electric power from the contacts to the tab ends.

10. The disc device for to a surface stimlation of an acupuncture point according to claim 9, and further comprising:
a lip on the base about at least the first layer.

11. The device for surface stimulation of an acupuncture point according to claim 2, wherein the gel overfills the holes.

12. The device for surface stimulation of an acupuncture point according to claim 1, wherein the tab ends of the second and third conductors project on a tab of the first layer for the connections to the stimulator.

13. The device for surface stimulation of an acupuncture point according to claim 12, wherein the holes about the circle are radially spaced from the central hole an integral multiple of an average cun.

14. The device for surface stimulation of an acupuncture point according to claim 13, and further comprising a stimulator, wherein the stimulator comprises:
a power and/or control unit having a base for receiving the first layer, the base having slots for receiving the tab ends in the use condition; and
contacts in the slots for providing electric power from the contacts to the tab ends.

15. The device for surface stimulation of an acupuncture point according to claim 12, wherein the gel overfills the holes.

16. The device for surface stimulation of an acupuncture point according to claim 1, wherein the gel overfills the holes.

17. The device for surface stimulation of an acupuncture point according to claim 16, wherein the holes about the circle are radially spaced from the central hole an integral multiple of an average cun.

18. The device for surface stimulation of an acupuncture point according to claim 17, and further comprising a stimulator, wherein the stimulator comprises:
a power and/or control unit having a base for receiving the first layer, the base having slots for receiving the tab ends in the use condition; and
contacts in the slots for providing electric power from the contacts to the tab ends.

19. The device for surface stimulation of an acupuncture point according to claim 1, wherein the holes about the circle are radially spaced from the central hole an integral multiple of an average cun.

20. The device for surface stimulation of an acupuncture point according to claim 1, wherein the layers are congruent discs.

21. In a device for surface stimulation of an acupuncture point, the improvements comprising:
a first electrically insulating layer;
a circular electrode film having one side on one side of the first layer and an opposite side;
an annular electrode film having one side on the side of the first layer and spaced a distance about the circular electrode film and an opposite side;
a pressure-sensitive electrically conductive adhesive layer on at least all of the opposite sides of the electrode films and the one side of the first layer across the distance the electrode films are spaced and adhered at least to the first layer, whereby an opposite side of the second layer adheres to a skin surface for use; and
electrical leads respectively to the circular and annular electrode films for connection to a stimulator.

22. The device for surface stimulation of an acupuncture point according to claim 21, wherein the second layer is transparent and the electrode films contrast visually with the first layer.

23. The device for surface stimulation of an acupuncture point according to claim 22, wherein the distance is an integral number of cun.

24. The device for surface stimulation of an acupuncture point according to claim 23, wherein the layers and electrode films are manually flexible.

25. The device for surface stimulation of an acupuncture point according to claim 22, wherein at least one of the electrodes is a silver/silver chloride polymer film.

26. The device for surface stimulation of an acupuncture point according to claim 22, wherein the layers and electrode films are manually flexible.

27. The device for surface stimulation of an acupuncture point according to claim 21, wherein the electrical leads are tab ends of the circular and annular electrode films.

28. The device for surface stimulation of an acupuncture point according to claim 21, wherein the layers and electrode films are manually flexible.

* * * * *